United States Patent [19]

Holton et al.

[11] Patent Number: 4,876,399

[45] Date of Patent: Oct. 24, 1989

[54] TAXOLS, THEIR PREPARATION AND INTERMEDIATES THEREOF

[75] Inventors: Robert A. Holton, Tallahassee, Fla.; Rouh-Rong Juo, North Billerica, Mass.; Richard Lowenthal, Tallahassee, Fla.

[73] Assignee: Research Corporation Technologies, Inc., Tucson, Ariz.

[21] Appl. No.: 115,665

[22] Filed: Nov. 2, 1987

[51] Int. Cl.$^4$ .............................................. C07C 35/37
[52] U.S. Cl. ................................... 568/817; 549/214; 549/215; 549/298; 549/332; 549/432; 549/433; 549/510; 549/544; 549/545; 556/436; 556/441; 556/443; 556/449; 560/39; 560/40; 560/256; 568/373; 568/861
[58] Field of Search .......................................... 568/817

[56] References Cited

U.S. PATENT DOCUMENTS 3,989,760 11/1976 Light et al. ..................... 568/817
4,453,000 6/1984 Schulte-Elte et al. .............. 568/817

Primary Examiner—Richard L. Raymond
Assistant Examiner—James H. Turnipseed
Attorney, Agent, or Firm—Scully, Scott, Murphy & Presser

[57] ABSTRACT

The present invention is directed to novel taxols useful as a chemotherapeutic agent. Moreover, the present invention is directed to the process of preparing taxols and various intermediates in said process. A key intermediate is this process is 2,5-dihydroxy-2-patchoulenes. Therefore the present invention is also related to said intermediate and the process for its preparation.

3 Claims, No Drawings

TAXOLS, THEIR PREPARATION AND INTERMEDIATES THEREOF

BACKGROUND OF THE INVENTION

1. Field of the Invention

The present invention is directed to various taxols, the process for preparing the same and novel intermediates thereof. In addition, the present invention relates to 2,5-dihydroxy-2-patchoulenes, which is not only a "bottleneck" intermediate in the synthesis of taxols but is also a flavoring agent.

2. Background of the Invention

In recent years, taxol has attracted much interest in both the biological and chemical arts. Taxol is a member of the taxane family of diterpenes, having the structure shown below:

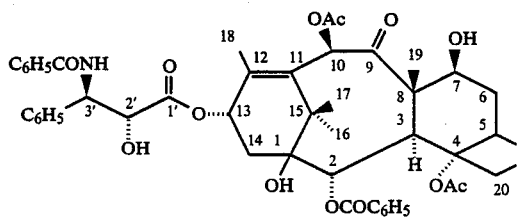

This compound was reported by Wani et al. in JACS, 93, 2325, (1971) to exhibit significant anti-tumor properties. More specifically, taxol shows strong cytotoxicity in KB cell structures and in several of the National Cancer Institute's in vivo screens, including P-388, L-1210 and P-1534 mouse leukemias, the B-16 melanocarcinoma, the CX-1 colon xenograft, the LX-1 lung xenograft and the MX-1 breast xenograft. In addition, taxol blocks cell replication in HeLa cells, especially in the mitotic phase of cell division. More specifically, it has been reported by Schiff et al in Nature, 277, 665 (1979) that taxol promotes the assembly of microtubule proteins responsible for the formation of spindles during cell division.

Because of its promising anti-cancer activity and its unusual structure and mechanism of action, taxol represents a prototype of a new class of chemotherapeutic agents. Consequently, it is presently undergoing clinical trials in both France and the United States.

Taxol is a natural product, which unfortunately is found in minute quantities in only the *Taxus brevifolia* species such as the Pacific yew tree and the *Taxus brevifolia* Nutt, from which it was first isolated. As more and more clinical experimentation is performed using taxols, it is becoming increasingly necessary to destroy more and more trees of the taxus species in order to isolate the compound. Consequently, there is a worldwide concern about the survival of the taxus species.

In view of the fact that taxol has significant commercial potential and there is a limited supply of taxol which is slowly being depleted, chemists in recent years have expended their energies in trying to find a viable synthetic route for the preparation of taxols. However, attempts have been unsuccessful. One difficulty in the synthesis lies in the preparation of the tricyclic carbon frame, pentadecene, which is shown below:

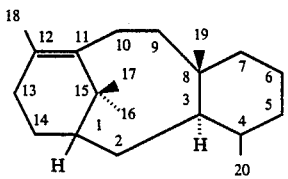

Robert Holton, in Jacs 106, 5731 (1984) reported the synthesis of taxanes A and B through the following scheme:

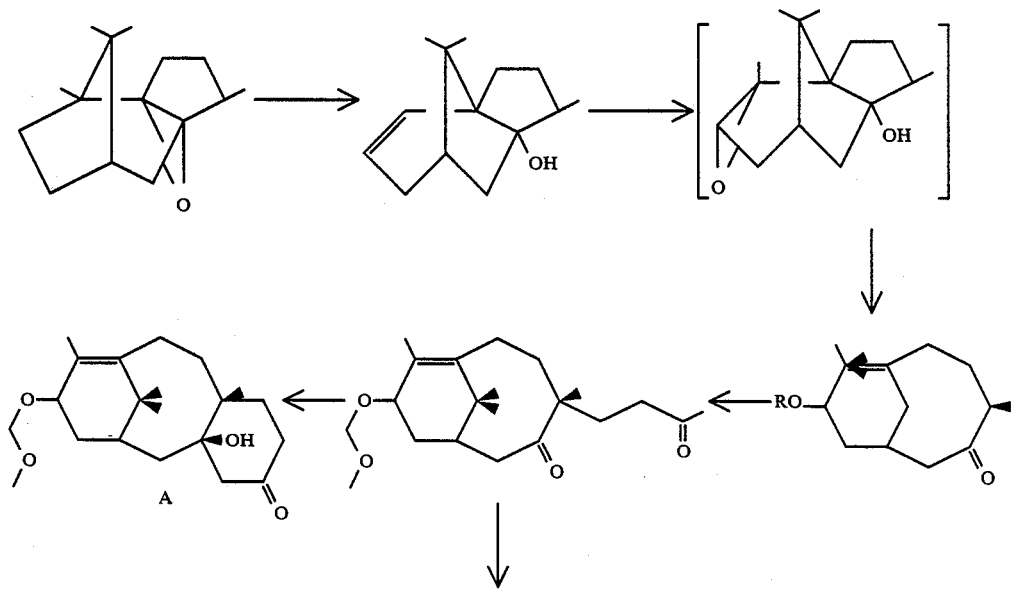

-continued

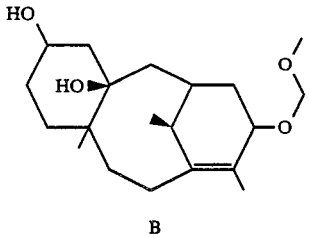

B

The major difficulty in the synthesis of taxol and other potential antitumor agents is the incorporation of the plethora of oxygen substituents present at positions 1, 2, 4, 5, 7, 9 and 10 of the ring system. It is believed that the key unlocking the mystery in the synthesis of taxols would be the discovery of a key intermediate. Through the use of this intermediate, it would be possible to form the paentadiene ring having a wide variety of different substituents at various positions. Consequently, the synthesis of taxols would be greatly facilitated. This need has been fulfilled by the discovery of the key intermediate by the present investigators.

SUMMARY OF THE INVENTION

The present invention is directed to the key intermediate in the synthesis of taxol and its use is not only synthesizing taxols but also other related taxanes. More specifically, the present invention is directed to a diol (2) and its first order derivatives, the structure of which is depicted hereinbelow. Its common name is 2,5-dihydroxy-2-patchoulene and its name according to the IUPAC rules is 4,10,11,11- tetramethyltricyclo [5.3.1.0]-undec-9-ene-2,5-diol:

In accordance with the present invention a process is provided for preparing taxols through the intermediary of the diol 2. Furthermore, the synthesis of taxols from the diol (2) proceeds through other intermediates. Consequently, the present invention is also directed to these other intermediates. Moreover, the present invention is directed to the process for preparing this diol. Furthermore, the present invention is directed to diols 2 and its first order derivatives, all of which can be utilized in the synthesis of taxol. In addition, this intermediate can be used in the synthesis of other non-natural taxols. Finally, the present invention is directed to these other taxols which also exhibits anti-tumor properties.

DETAILED DESCRIPTION

The present invention is directed to taxols having the following structural formula:

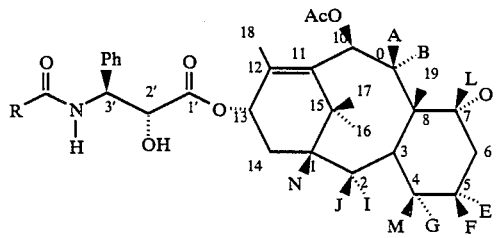

wherein
A and B are independently hydrogen or lower alkanoyloxy or
A and B together form an oxo;
L and D are independently hydrogen or hydroxy;

E and F are independently hydrogen or lower alkanoyloxy or;
E and F together form an oxo;
G is hydrogen or lower alkanoxy or lower aklanoyloxy or aroyloxy or
G and M together form an oxo or methylene or
G and M together form an oxocyclopropyl ring or
M and F together form an oxocyclobutyl ring;
J is hydrogen or aroyloxy or lower alkanoyloxy or
I is hydrogen or aroyloxy; or
I and J taken together form an oxo; and
N is hydrogen, hydroxy or lower alkoxy and
R is aryl, lower alkyl or lower alkenyl.

The alkyl groups, either alone or with the various substituents defined hereinabove are preferably lower alkyl containing from one to about six carbon atoms in the principal chain and up to about 10 carbon atoms. They may be straight or branched chain and include methyl, ethyl, propyl, isopropyl, butyl, isobutyl, tert-butyl, aryl, hexyl, and the like.

Examplary alkanoyloxy include acetate, propionate, butyrate, valarate, isobutyrate and the like. The more preferred alkanoyloxy is acetate.

The aryl moieties described hereinabove or hereinbelow, either alone or with various substituents contain from about 6 to about 10 carbon atoms and include phenyl, α- naphthyl or β-naphthyl, etc. Phenyl is the more preferred aryl.

The lower alkenyl groups contain from 2 to about 6 carbon atoms in the principal chain and up to a total of about 10 carbon atoms. They may be straight or branched chain and include ethenyl, 1-propenyl, isopropenyl, 1-butenyl, 2-butenyl, 3-butenyl, isobutenyl and the like.

Preferred value of the substituents A, B, L, D, G, F, G, M, I, J, and N are enumerated herein below:
A is hydrogen;
B is hydrogen, or acetate or
A and B together from an oxo;
L is hydrogen or hydroxy;
D is hydrogen or hydroxy;
E is hydrogen, or acetate or
E and F together form an oxo or
M and F together form an oxocyclobutyl ring;
G is hydrogen or acetate or
G and M together form an oxo or methylene or oxocyclopropyl ring;
J is hydrogen;
I is hydroxy or aroyloxy, such as benzoyloxy or
I and J together form an oxo; and
N is hydrogen, hydroxy or lower alkanoyloxy Examplary compounds within the generic formula are depicted hereinbelow:

-continued
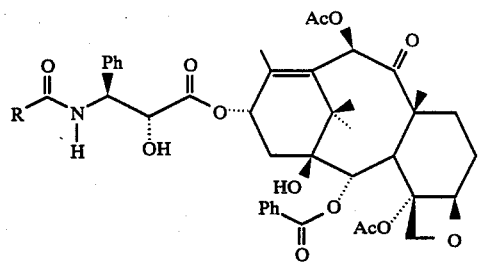
15
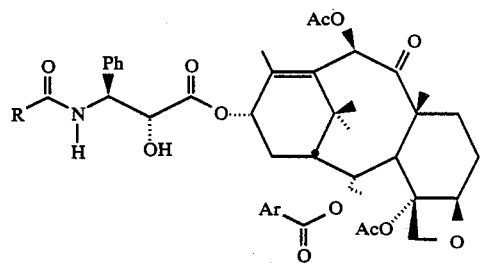
21
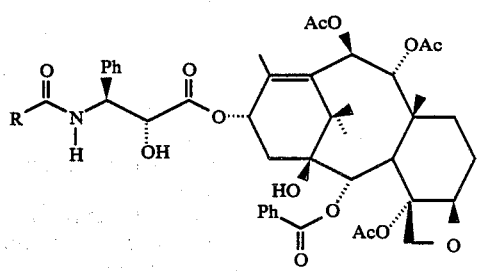
16
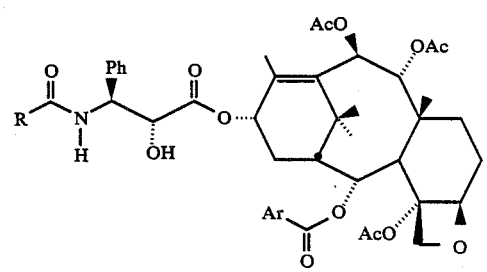
22
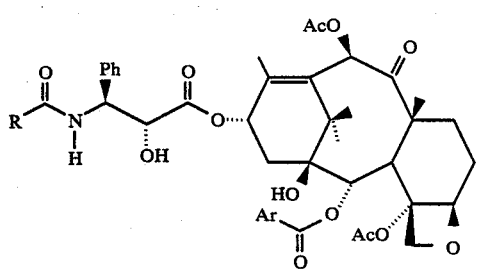
17
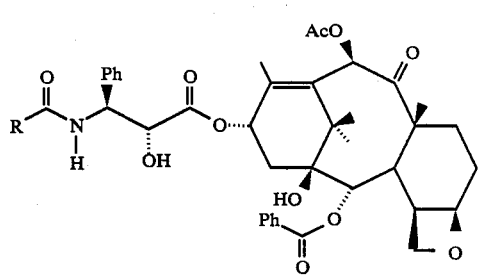
23
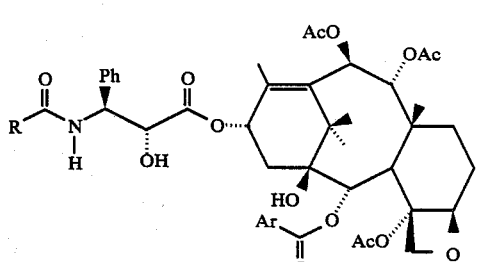
18
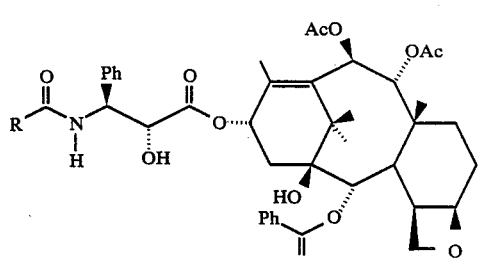
24
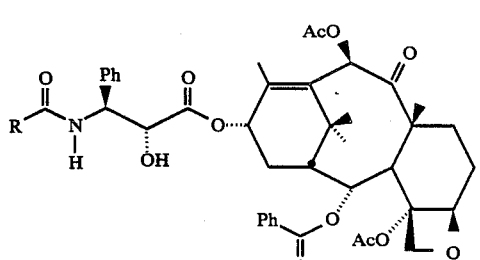
19
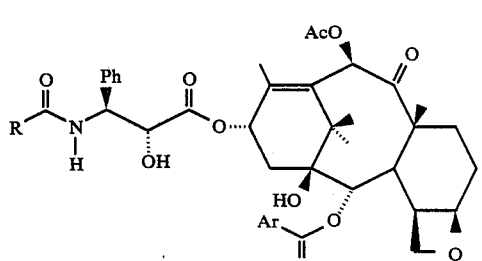
25
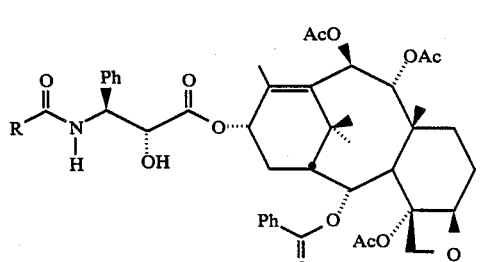
20
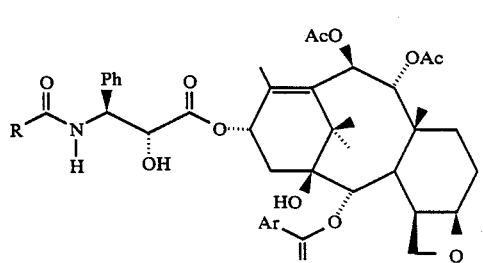
26

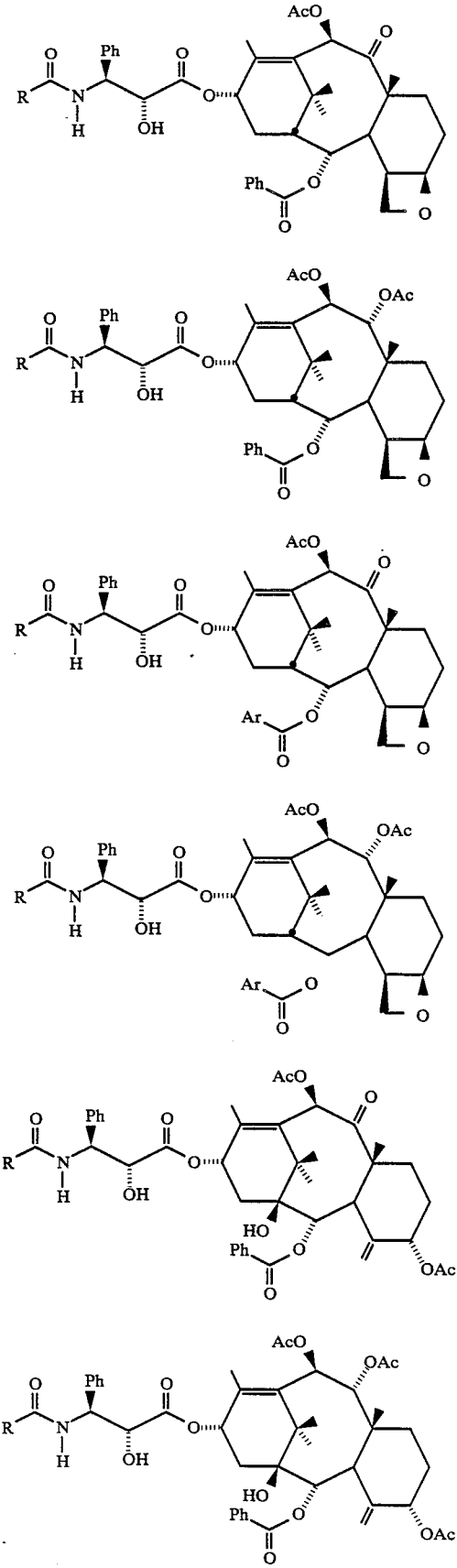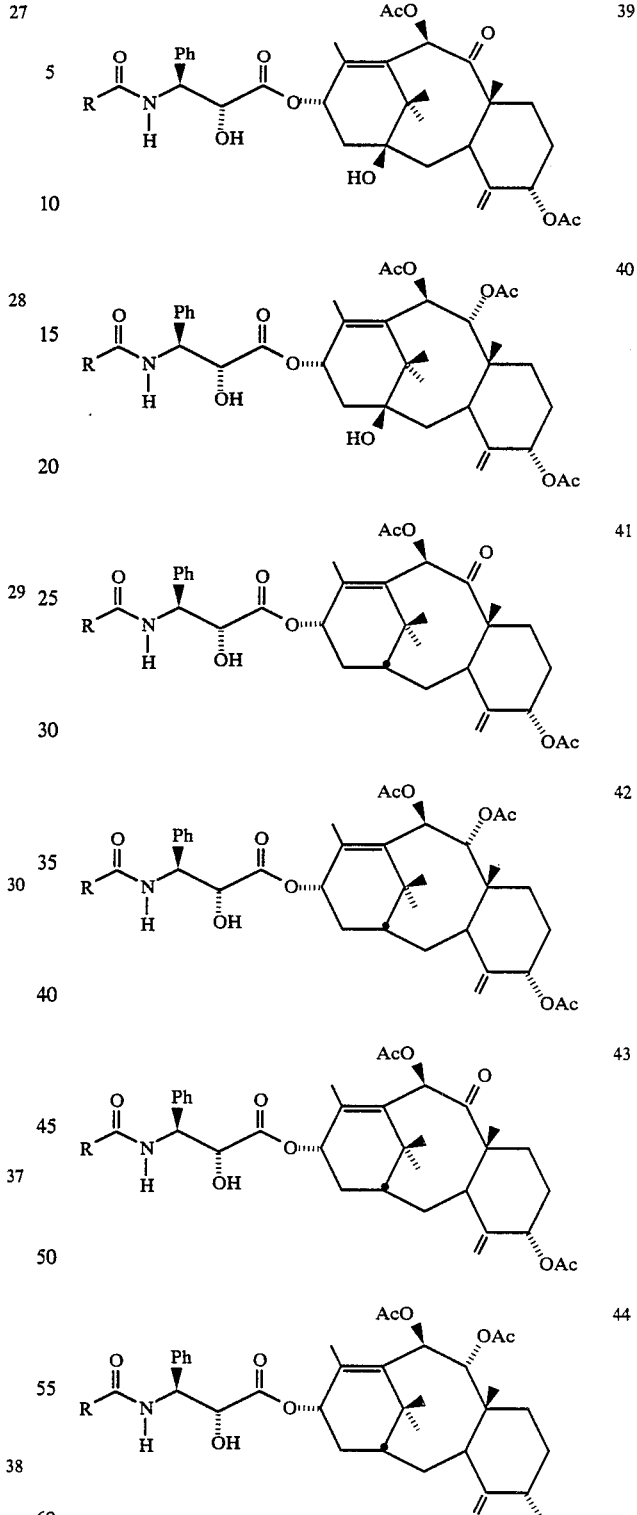
The present invention also relates to the key intermediates diol 2 and its first order derivatives thereof having the structure given below:

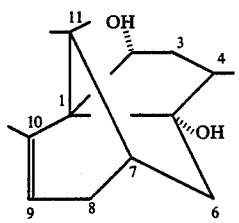

2

The numbers in the structural formula hereinabove correspond to the ring positions in the diol 2. By first order derivatives it is meant that additional variations in the structural formula hereinabove can be effected without significantly altering the utility of the diol as described hereinabove or hereinbelow. For example, the hydroxy group at position 2 of the ring can have protecting groups thereon, such as ethers, i.e., methoxy, benzyloxy; esters, such as acetates; carbonates, such as methyl carbonates, and silyl ethers, such as trimethyl silyl, triethyl silyl; and the like. A variety of protecting groups for the hydroxy and the synthesis thereof is found may be found in "Protective Groups in Organic Synthesis" by T.W. Green, John Wiley and Sons, 1981.

Since the diol (2) has several asymmetric carbons, it is known to those skilled in the art that the compounds of the present invention having asymmetric carbon atoms may exist in racemic or optically active forms. All of these forms are contemplated within the scope of the invention. More specifically, the present invention includes enantiomers, diastereomers, racemic mixtures and other mixtures thereof.

The importance of diol 2 as a key intermediate was first recognized in the synthesis of a simpler cogener of taxol called taxusin, the scheme of which is depicted hereinbelow:

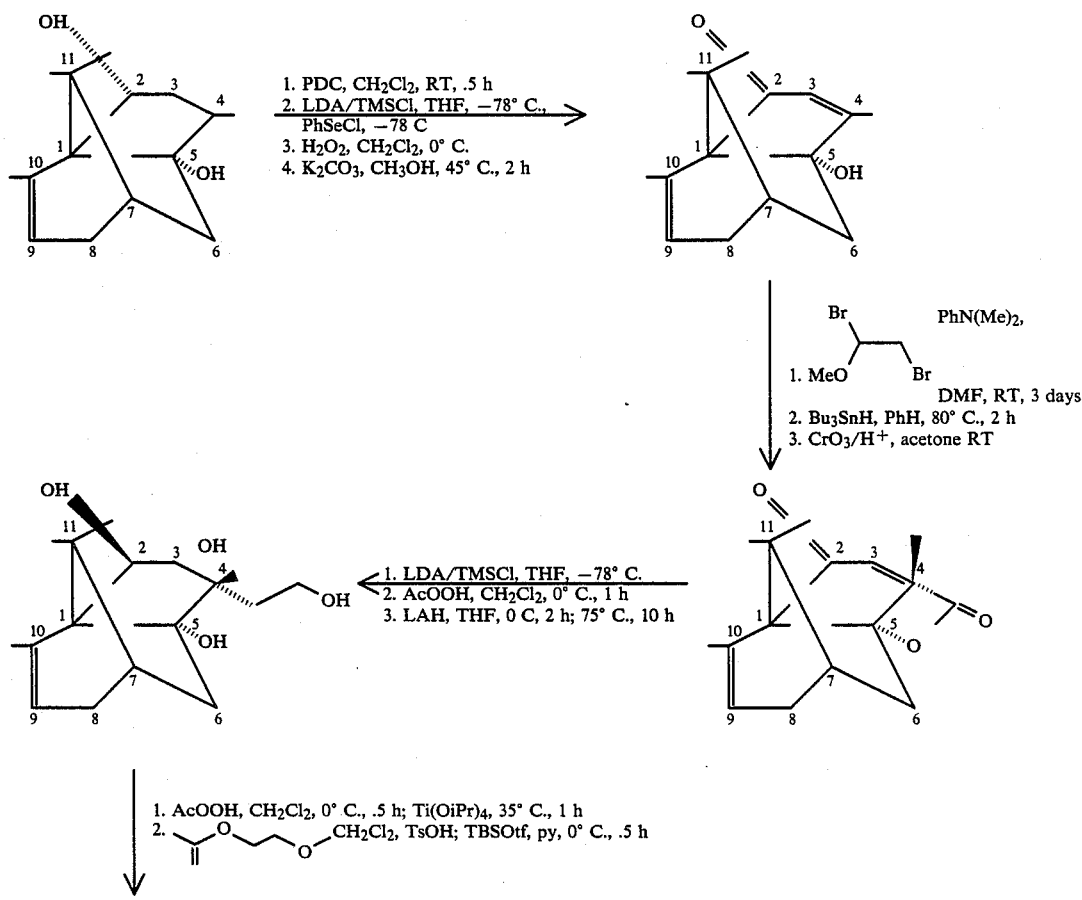

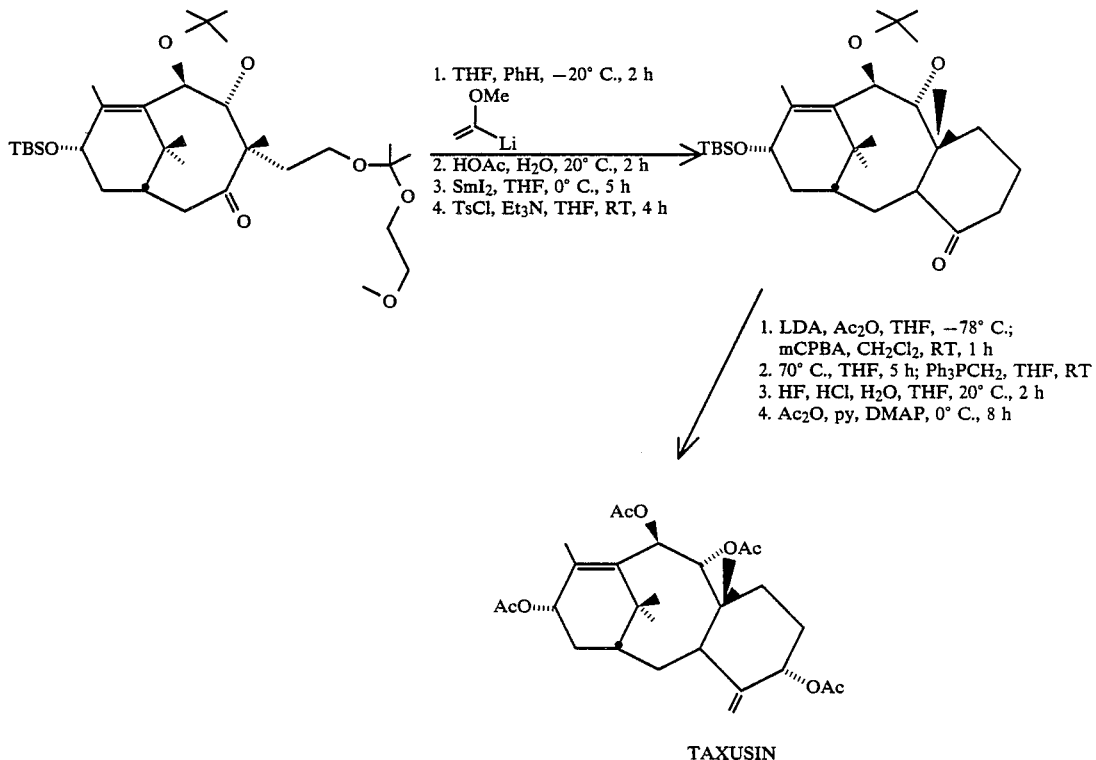
TAXUSIN
An exemplary synthesis of taxol is depicted hereinbelow. Although the present scheme is directed to the natural product taxol, the scheme can be used with modifications that are obvious to one skilled in the art to prepare the other synthetic taxols contemplated within the present invention.

CONVERSION OF DIOL 2 TO TAXOL 1
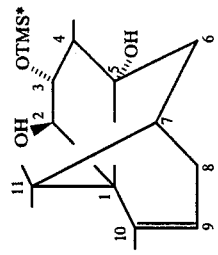
2
1. PDC, CH$_2$Cl$_2$, RT, .5 h
2. LDA/TMSCl, THF, −78° C.
3. mCPBA, CH$_2$Cl$_2$, RT, .5 h
4. LiAlH$_4$, Et$_2$O, 0° C.
→
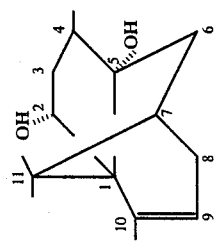
3
1. TBSOTf, pyridine, 0° C.
2. AcOOH, Ti(OiPr)$_4$, CH$_2$Cl$_2$, 25° C.
3. DPSOTf, pyridine, 0° C.
→
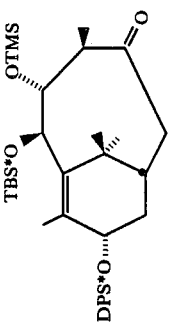
4
← 1. LDA/PhSeSePh, THF, −78° C.
2. mCPBA, CH$_2$Cl$_2$, 0° C.
3. H$_2$O$_2$, NaOH, 25° C.
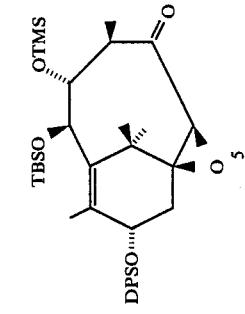
5
1. Li(sBu)$_3$BH, THF, −78° C.
2. a. MeO—C(Li)=CH—CH=CH—OMe, THF, −20° C.
   b. PhCOCl, CH$_2$Cl$_2$, py; c. HF, py, 0° C, 10 min
3. PDC, CH$_2$Cl$_2$; K$_2$CO$_3$, tBuOH, 0° C.
→

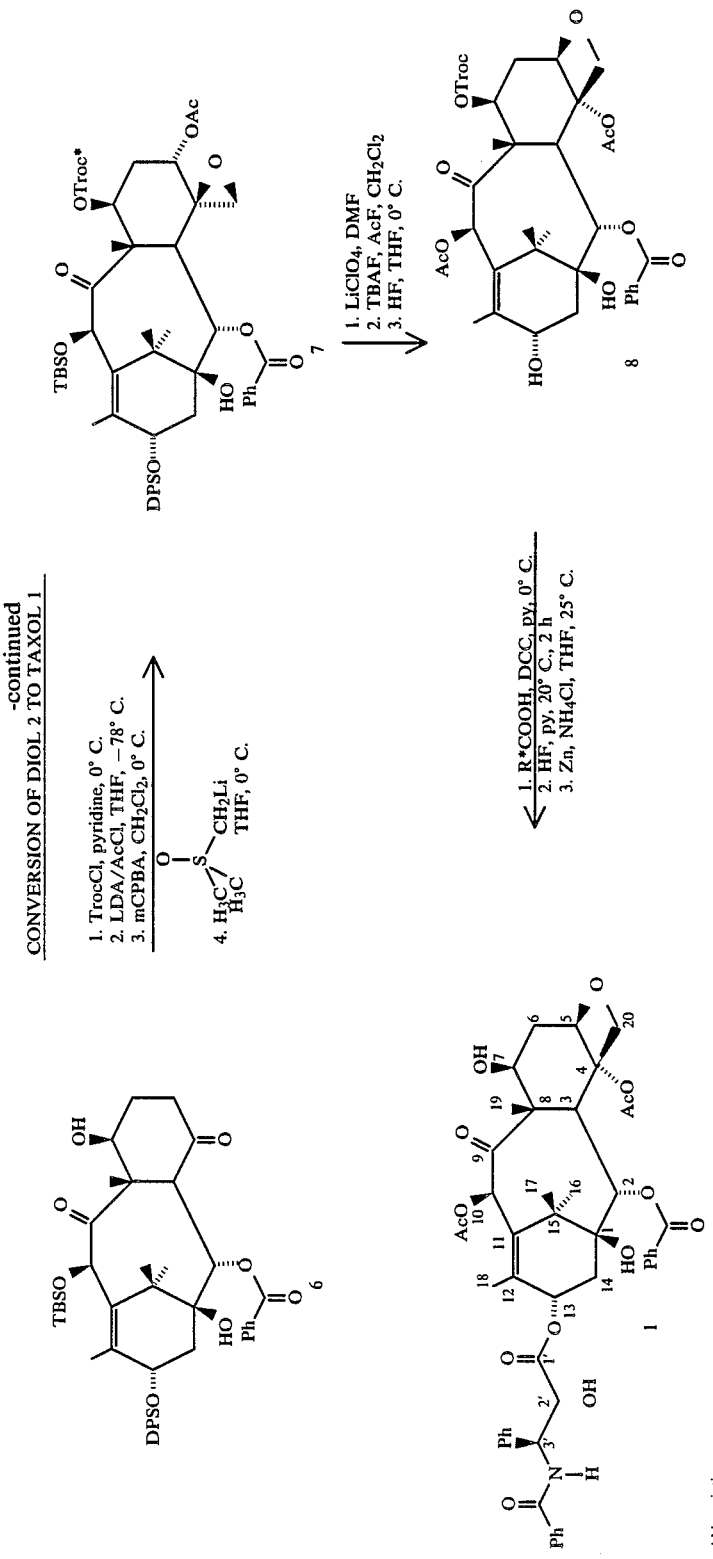

The intermediate diol 2 can in turn be prepared from commercially available products, as shown in the scheme below:

PREPARATION OF DIOL 2 FROM PATCHINO

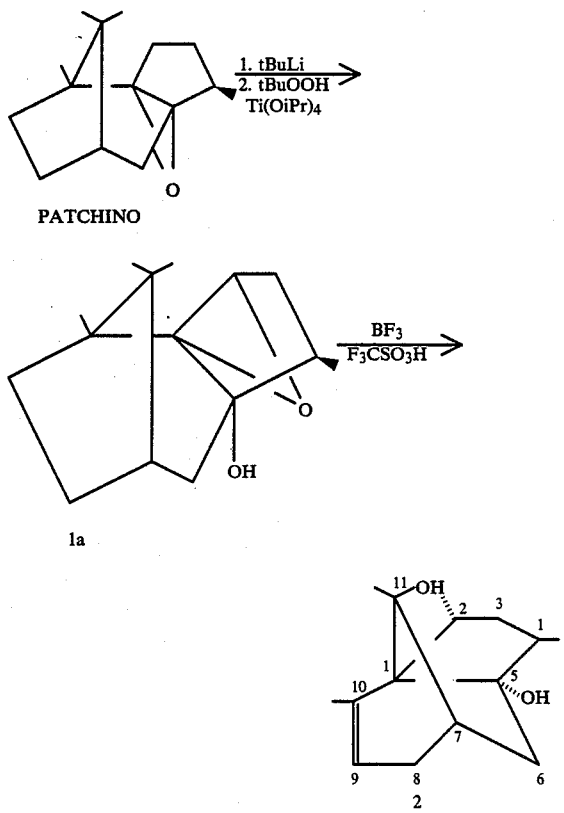

The starting material, patchino, is a natural product which is more commonly known as B-patchouline epoxide. Patchino which is commercially available can be obtained from natural sources, from rearrangement of patchouli alcohol followed by epoxidation or commercially from IFF.

The patchino is first reacted with an organometallic, such as lithium t-butyl followed by oxidation with an organic peroxide, such as t-butylperoxide in the presence of titanium tetra-isopropoxide to form the tertiary alcohol 1a.

The tertiary alcohol 1a is then reacted with a Lewis acid, such as boron trifluoride at low temperature, in the range from 40° C. to -100° C.; in the presence of an acid, such as trifluoromethane sulfonic acid.

The reaction for the formation of diol 2 from 1a is sensitive to conditions. The reaction proceeds at low temperatures, but is preferred at -80° C. However, the yield is significantly increased when the trifluoromethane sulfonic acid is additionally added.

The following example depicts in more detail the formation of the diol 2 from the epoxide 1a:

EXAMPLE 1

Preparation of Diol 2 from Epoxide 1a Experimental

To a rapidly stirred (mechanical stirrer) solution of 7.56 g (0.032 mol) of epoxide 1a in 756 mL of rigorously dry methylene chloride (0.042 M) at −80° C. in an elongated cylindrical Mortan flask (situated inside a well insulated Dewar flask charged with dry ice/acetone) was added via syringe over a period of 1h a solution of 7.88 mL (0.064 mol) of boron trifluoride etherate and 0.71 mL (0.008 mol) of trifluoromethane sulfonic acid in 40 mL of rigorously dry methylene chloride (the boron trifluoride etherate/trifluoromethane sulfonic acid solution must be added down the side of the flask). The mixture was rapidly stirred at −80° C. for an additional 21 h before the addition of 13.4 mL (0.096 mol) of triethylamine via syringe over a period of 0.5 h. The −80° C. mixture was rapidly poured into 2000 mL of a rapidly stirred saturated aqueous sodium bicarbonate solution which had been precooled to 0° C. The layers were separated and the methylene chloride solution was washed three times with 500 mL of saturated aqueous sodium bicarbonate solution. Each sodium bicarbonate wash solution was reextracted two times with 100 mL of methylene chloride. The combined methylene chloride solutions were dried over anhydrous sodium sulfate and concentrated under reduced pressure to give 7.61 g of crude product. The crude product was purified by filtration through a plug of silica gel using ethyl acetate/hexane as eluant to provide 5.44 (72%) of crystalline 2 and 1.814 g (24%) of recovered 1a.

Recrystallized 2 had the following physical properties: m.p. 95°-96° C.; $[\alpha]_{Hg} = 54°$.

Diol 2 is also a flavor or fragrance ingredient. It has a pleasant but somewhat subtle musky odor containing combining elements of wintergreen and ambergest. As such, it can be used to add fragrance in perfumes, lotions, creams, colognes, powders, soaps and detergents. Thus a fragrant composition can be prepared comprising an effective fragrant amount of the diol 2 in association with a carrier, such as alcohols, talcum powder, soap chips, detergents powder and the like.

For example, in order to achieve the effects of the present invention, diol 2 is generally used as an additive in perfumes in amounts ranging from about 10% to about 15% by weight to provide material with an excellent musky aroma. Moreover, it can be added to cologne and handkerchief perfume in concentrations ranging from about 3% to about 10% by weight to add depth to the aroma.

EXAMPLE 2

The diol 2 can be used to prepare a rose perfume as follows:

| | |
|---|---|
| Rhodinol | 30 g |
| B—phenylethyl alcohol | 25 g |
| Bulgarian rose oil | 15 g |
| Guaiol acetate | 15 g |
| Diol 2 | 15 g |
| Total | 100 g |

An aqueous gel-type odorous agent is prepared by using this formulated perfume and carrageenin gel. This agent is suitable as an oriental rose perfume for interior use.

Diol 2 can be formulated with detergent powders, dusting powders and soaps to provide an excellent subtle and pleasing aroma. The diol 2 is generally added in amounts ranging from about 0.001 to about 1% of the detergent bath powders or soaps as shown in the following formulation examples.

EXAMPLE 3

An exemplary procedure for the formulation of a detergent is as follows:

0.25g of 2 which is prepared according to the procedure of Example 1 is added to 100g of detergent powder. The product is mixed until homogeneous.

EXAMPLE 4

An exemplary procedure for the formulation of a bath powder is as follows:

250g of talcum powder is added to 1 gram of diol 2, prepared according to the procedure of Example 1. The resulting product is mixed in a ball mill until homogeneous.

EXAMPLE 5

An exemplary procedure for the formulation of soap is as follows:

1g of 2 prepared according to the procedure of Example 1 is added to 100g of ivory soap chips, and is mixed together until homogeneous. The resulting homogeneous mixture is heated at 180° C. for 3 hours, placed into soap molds and allowed to cool. When cool, the soap has a subtle but excellent aroma.

The above preferred embodiments and examples are given to illustrate the scope and spirit of the present invention. These embodiments and examples will make apparent to those skilled in the art other embodiments and examples. These other embodiments are examples are within the contemplation of the present invention. Therefore, the present invention should be limited only by the appended claims.

What is claimed:

1. A diol of the formula:

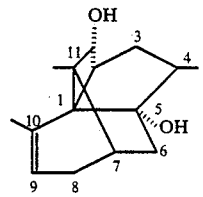

2. The enantiomers of the compound of claim 1.
3. The diastereomers of the compound of claim 1.